(12) United States Patent
Scheffler

(10) Patent No.: US 10,197,525 B2
(45) Date of Patent: Feb. 5, 2019

(54) PULSED POTENTIAL GAS SENSORS

(71) Applicant: MSA TECHNOLOGY, LLC, Cranberry Township, PA (US)

(72) Inventor: Towner Bennett Scheffler, Butler, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 451 days.

(21) Appl. No.: 14/976,034

(22) Filed: Dec. 21, 2015

(65) Prior Publication Data

US 2017/0176377 A1 Jun. 22, 2017

(51) Int. Cl.
*G01N 27/404* (2006.01)
*G01N 27/30* (2006.01)

(52) U.S. Cl.
CPC ......... *G01N 27/4045* (2013.01); *G01N 27/30* (2013.01)

(58) Field of Classification Search
CPC ............. G01N 27/48; G01N 27/49; G01N 27/404–27/4078
See application file for complete search history.

(56) References Cited

U.S. PATENT DOCUMENTS

| | | | |
|---|---|---|---|
| 4,500,391 A * | 2/1985 | Schmidt | G01N 27/48 204/406 |
| 5,202,637 A | 4/1993 | Jones | |
| 5,273,640 A | 12/1993 | Kusanagi | |
| 5,554,269 A * | 9/1996 | Joseph | G01N 27/4065 204/424 |
| 5,611,909 A | 3/1997 | Studer | |

(Continued)

FOREIGN PATENT DOCUMENTS

| | | |
|---|---|---|
| DE | 4212792 A1 | 10/1993 |
| EP | 0039549 A2 | 11/1981 |

(Continued)

OTHER PUBLICATIONS

Buchberger, Wolfgang; Elektochemische Analyseverfahren, Spektrum Akademischer Verlag GmbH, Heidelberg-Berlin, pp. 78-89.

(Continued)

*Primary Examiner* — Gurpreet Kaur
(74) *Attorney, Agent, or Firm* — Bartony & Associates, LLC

(57) ABSTRACT

A method of operating an electrochemical gas sensor, which includes at least one working electrode including an electrocatalyst and having a ratio of total electrochemically accessible surface area to geometrical surface area of at least 2:1, includes alternatively biasing a potential of the at least one working electrode to a first potential at which the electrocatalyst is active to catalyze a redox reaction of a first target gas and to a second potential, different from the first potential, at which the electrocatalyst is substantially inactive to catalyze the redox reaction of the first target gas, a plurality of times, measuring a first output signal arising from the redox reaction of the first target gas at the first potential, and deconvoluting the first output signal while the at least one working electrode is biased at the first potential to separate a portion of the first output signal arising from non-faradaic current to determine a concentration of the first target gas.

19 Claims, 16 Drawing Sheets

(56) References Cited

U.S. PATENT DOCUMENTS

| | | | |
|---|---|---|---|
| 5,667,653 | A | 9/1997 | Schneider |
| 6,076,389 | A | 6/2000 | Kaneko |
| 6,200,443 | B1 | 3/2001 | Shen |
| 6,344,174 | B1 | 2/2002 | Miller |
| 6,428,684 | B1 | 8/2002 | Warburton |
| 6,896,781 | B1 | 5/2005 | Shen |
| 7,413,545 | B2 | 8/2008 | Scheffler |
| 7,413,645 | B2 | 8/2008 | Scheffler |
| 2005/0045493 | A1 | 3/2005 | Mahurin |
| 2013/0186776 | A1* | 7/2013 | Scheffler ................ G01N 27/26 205/785.5 |

FOREIGN PATENT DOCUMENTS

| | | |
|---|---|---|
| EP | 0269794 A2 | 6/1988 |
| EP | 0990895 A2 | 4/2000 |
| EP | 1039293 A1 | 9/2000 |
| WO | WO8902593 A1 | 3/1989 |
| WO | WO2017112213 A1 | 6/2017 |

OTHER PUBLICATIONS

Cao, Z. and Stetter, Jr., "The Properties and Applications of Amperometric Gas Sensors," Electroanalysis, 4(3), 253-266 (1992).

J. Osteryoung and K. Hasebe, "Pulse Polarography—Theory and Application," Review of Polarography, 1976, 1:22, 1-25.

A. J. Bard and L. R. Faulkner, Electrochemical Methods (Wiley: New York), 1980, Chapter 5, pp. 136-199.

P. T. Kissinger and W. R. Heineman, Laboratory Techniques in Electroanalytical Chemistry (Marcel Dekker: New York), 1984, pp. 143-161.

Tilak, B. V., Rader, C. G., & Rangarajan, R., J. Electrochem. Techniques for Characterizing Porous Electrodes, J. Electrochem. Soc., 124, (1977), pp. 1879-1886.

J. Osteryoung and M. M. Murphy, "Normal and Revers Pulse Voltammetry at Small Electrodes," Microelectrodes: Theory and Applications, Nato ASI Series, Series E: Applied Sciences, 197, (1991), pp. 123-138.

Hobbs, B. S., Tantram, A. D. S., & Chan-Henry, R., Liquid Electrolyte Fuel Cells. In Techniques and Mechanisms in Gas Sensing; Norris, J. O. W. & Williams, D. E., Eds, Adam Hilger: Bristol (1991), pp. 161-188.

Stetter, J. R. & Li, J., Amperometric Gas Sensors, Chem Rev, 108, (2008), pp. 352-366.

Trasatti, S. & Petrii, O. A., Real Surface Area Measurements in Electrochemistry, Pure & Appl. Chem., vol. 63, No. 5, (1991), pp. 711-734.

Gu, P. Bai, L., Gao, L., Brousseau, R., & Conway, B. E., Problems in the Determination of Adsorption Behaviour of Intermediates in Faradaic Reactions: Distintion Between Double Layer and Adsorption Capacitance of Electrocatalysts Determined from fast Potential Relaxation Transients, Electrochimica Acta, vol. 37, No. 12, (1992), pp. 2145-2154.

Bai, L., Gao, L., & Conway, B. E., Problem of in situ Real-area Determination in Evaluation of Performance of Rough or Porous, gas-evolving Electrocatalysts, J. Chem. Soc. Faraday Trans., 89(2), (1993), 235-242.

Hills, G. J., & Payne, R., Improved Method for Measuring the Souble Layer Capacity at a Dropping Mercury Elecgtrode, Trans. Faraday Soc., 61, (1965), 316-325.

\* cited by examiner

PULSED POTENTIAL GAS SENSORS

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Pulsed electrochemical techniques are well known. Pulsed voltammetric techniques may lower detection limits in electrochemical analysis. In a typical electrochemical cell, one observes two types of current flow, which are termed "Faradaic" and "non-Faradaic" currents. Faradaic currents result from the electrochemical conversion of one chemical substance to another, either oxidation or reduction, and are generalized by:

$$Ox + ne^- \rightarrow Red \quad (1)$$

The symbol, "$e^-$" in equation (1) represents the electrons transferred in the electrochemical conversion and n is the number of electrons. The transferred electrons in the electrochemical conversion give rise to the output/signal current produced by the sensor when it is exposed to the target gas. On the other hand, non-Faradaic currents result from rearrangement of ions present in the electrolyte of the sensor very close to the electrode surface and other processes such as adsorption and desorption of ions. Non-Faradaic currents do not contribute to the analytical signal of the sensor, but result in the noise observed in the sensor signal when no target gas is present. The above discussion applies to a sensor operated at a constant potential.

In the absence of target gas, if the potential applied to the working electrode of a sensor is suddenly changed, an instantaneous current will flow in the sensor that is non-Faradaic. This current has an exponential time dependence and will decrease toward zero current according to:

$$i_c = \frac{E}{R_s} e^{-t/R_s C_{WE}} \quad (2)$$

where $i_C$ is the observed current (the charging current), t is the time after the potential change, E is the magnitude of the potential change, $R_S$ is the solution resistance, and $C_{WE}$ is the capacitance of the working electrode (which is directly dependent upon the electrochemically active/accessible area of the working electrode). This behavior is shown in FIG. 1A.

If the potential change is applied to the working electrode when target gas is present, and the potential of the working electrode is such that the target gas undergoes a Faradaic reaction (is oxidized or reduced), the observed current is provided by:

$$i_T = i_c + i_F \quad (3)$$

Where $i_T$ is the sum of the charging current, $i_C$, and the Faradaic current, $i_F$. In the case of amperometric electrochemical sensors, $i_F$ is often expressed as:

$$i_F = nFAC\frac{D}{x} \quad (4)$$

In equation (4), n is the number of electrons involved in the electrochemical reaction, F is Faraday's constant, A is the electrochemically active/accessible area of the working electrode C is the concentration of the target gas, D is the diffusion coefficient of the target gas, and x is the distance the target gas must diffuse to reach the electrochemically active surface of the working electrode. Equation (4) is obtained by considering Fick's laws of diffusion. Equation (4) indicates that the Faradaic current is directly dependent upon the concentration of the target gas and is assumed insensitive to time, which is an approximation. The value of D/x (the solution to Fick's laws under the physical conditions of the experiment) will always be time dependent. However its value quickly reaches a steady state condition for amperometric electrochemical gas sensors, and is essentially independent of time.

Various discussions and derivations of the theory of pulsed voltammetry or polarography indicate that the motivations behind the development of these techniques include increasing the analytical sensitivity of these methods by separating, in time, the charging current and the Faradaic current. There are at least three critical criteria generally accepted to be required for the success of pulsed voltammetric methods: First, the potential pulse should be small. For maximum fidelity, the pulse magnitude should be less than about 0.059/n volts (at 25 C), where n is the number of electrons transferred in the electrochemical reaction (see equation (1)). Second, the time between pulses should be long, allowing the charging current to decay to small values. For classically sized analytical electrodes (1 cm²) or smaller, the wait time can be on the order of several seconds (that is, longer than 5 seconds and more typically several hundred seconds). Third, the electrode area should be minimized. Pulsed voltammetric techniques were first developed for use in electroanalytical procedures with macro electrodes for which the geometric area closely approximated the electrochemically active/accessible area. See, for example, A. J. Bard and L. R. Faulkner, *Electrochemical Methods* (Wiley: New York), 1980, 183; P. T. Kissinger and W. R. Heineman, *Laboratory Techniques in Electroanalytical Chemistry* (Marcel Dekker: New York), 1984, 143; J. Osteryoung and M. M. Murphy, "Normal and Revers Pulse Voltammetry at Small Electrodes," *Microelectrodes: Theory and Applications*, 1991, 123-138; and J. Osteryoung and K. Hasebe, "Pulse Polarography—Theory and Application," *Review of Polarography*, 1976, 1:22, 1-25. The desire to increase the sensitivity of these techniques (as well as other motivations) led to the development of micro- and ultramicro-electrodes; electrodes with areas of approximately 1 μm².

All of these developments generally had one goal in mind; minimizing the charging current with respect to the Faradaic current. Pulsed voltammetric techniques lowered the typical useful concentration range of electroanalytical methods from parts-per-thousand ($10^{-3}$) to parts per million (ppm, $10^{-6}$), and lower.

The above discussion applies to classic solution-oriented electroanalytical techniques. Amperometric electrochemical gas sensors differ in several important ways which have been understood to severely limit or eliminate the usefulness of pulse techniques in such an application.

SUMMARY

In one aspect, a method of operating an electrochemical gas sensor, which includes at least one working electrode including an electrocatalyst and having a ratio of total electrochemically accessible surface area to geometrical surface area of at least 2:1, includes alternatively biasing a potential of the working electrode to a first potential at which the electrocatalyst is active to catalyze a redox reaction of a first target gas and to a second potential, different from the first potential, at which the electrocatalyst is substantially inactive to catalyze the redox reaction of the first target gas, a plurality of times, measuring a first output signal arising from the redox reaction of the first target gas at the first potential, and deconvoluting the first output signal while the working electrode is biased at the first potential to separate a portion of the first output signal arising from non-faradaic current to determine a concentration of the first target gas.

The method may further include deconvoluting the first output signal while the working electrode is biased at the first potential to separate the portion of the first output signal arising from non-faradaic current to determine a concentration of the first target gas each of the plurality of times the potential of the working electrode is biased to the first potential.

In a number of embodiments, the ratio of total electrochemically accessible surface area to geometrical surface area is at least 10:1, at least 200:1 or at least 500:1. In a number of embodiments, the measured output signal is deconvoluted after at least 95% or at least 99% of a time period for alternating between the first potential and the second potential is past. The time period for alternating between the first potential and the second potential may, for example, be less than 5 seconds, no more than 1 second, no more than 500 milliseconds or no more than 100 milliseconds.

In a number of embodiments, the electrocatalyst catalyzes a redox reaction of a second target gas, different from the first target gas, at the second potential and the electrocatalyst is substantially inactive to catalyze the redox reaction of the second target gas at the first potential. The method may further include measuring a second output signal arising from the redox reaction of the second target gas at the second potential, and deconvoluting the second output signal while the working electrode is biased at the second potential to separate a portion of the second output signal arising from non-faradaic current to determine a concentration of the second target gas.

The method may, for example, include deconvoluting the first output signal while the working electrode is biased at the first potential to separate the portion of the first output signal arising from non-faradaic current to determine a concentration of the first target gas each of the plurality of times the potential of the working electrode is biased to the first potential and deconvoluting the second output signal while the working electrode is biased at the second potential to separate the portion of the second output signal arising from non-faradaic current to determine a concentration of the second target gas each of the plurality of times the potential of the working electrode is biased to the second potential.

In a number of embodiments, the measured first output signal is deconvoluted while the working electrode is biased at the first potential after at least 95% or 99% of a time period for alternating between the first potential and the second potential is past and the measured second output signal is deconvoluted while the working electrode is biased at the second potential after at least 95% or 99% of a time period for alternating between the first potential and the second potential is past.

In a number of embodiments, deconvoluting the output signal while the working electrode is biased at the first potential or second potential to separate a portion of the first output signal or second output signal arising from non-faradaic current comprises subtracting a baseline non-faradaic signal determined in the absence of the target gas. For example, deconvoluting the first output signal while the working electrode is biased at the first potential to separate a portion of the first output signal arising from non-faradaic current may include subtracting a baseline non-faradaic signal determined in the absence of the first target gas, and deconvoluting the second output signal while the working electrode is biased at the second potential to separate a portion of the second output signal arising from non-faradaic current may include subtracting the baseline non-faradaic signal determined in the absence of the first target gas.

In another aspect, an electrochemical gas sensor includes at least one working electrode comprising an electrocatalyst and having a ratio of total electrochemically accessible surface area to geometrical surface area of at least 2:1, circuitry to bias the working electrode to a first potential at which the electrocatalyst catalyzes a redox reaction of a first target gas and bias the working electrode to a second potential, different from the first potential, at which the electrocatalyst is substantially inactive to catalyze the redox reaction of the first target gas, and a system to deconvolute an output signal when the working electrode is biased at the first potential to separate a portion of the output signal arising from non-faradaic current to determine a concentration of the first target gas.

The present devices, systems, and methods, along with the attributes and attendant advantages thereof, will best be appreciated and understood in view of the following detailed description taken in conjunction with the accompanying drawings.

DETAILED DESCRIPTION

Figure 1A:
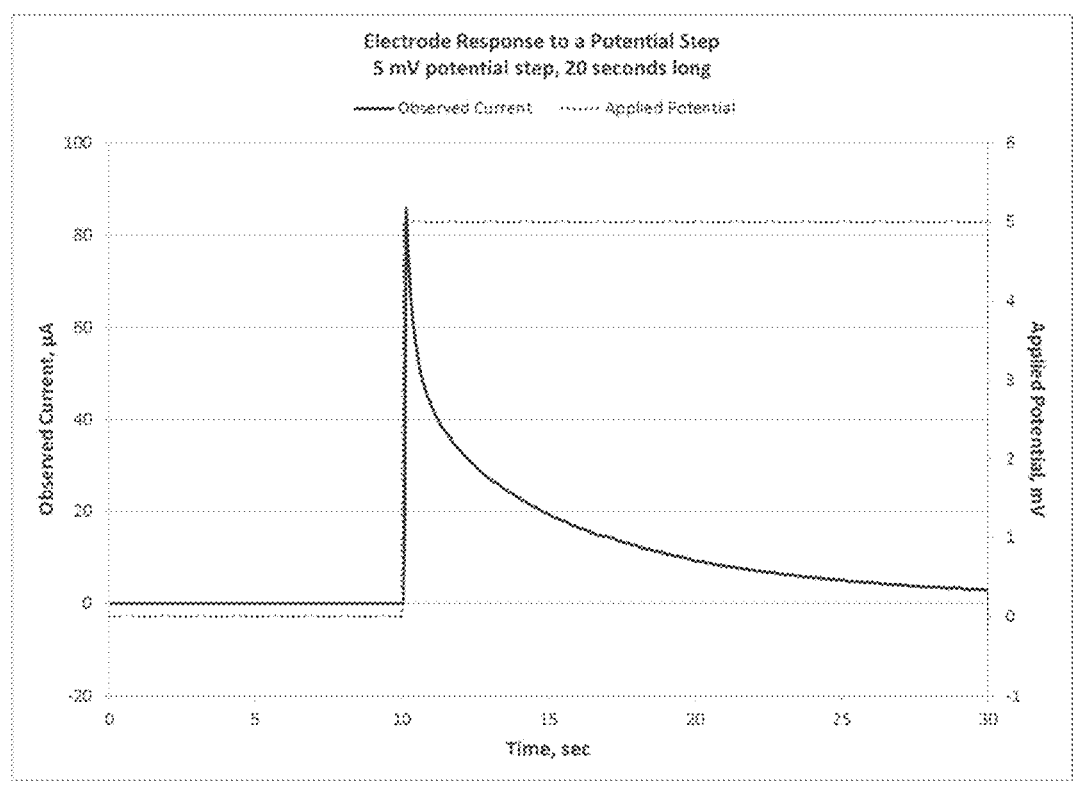
FIG. 1A illustrates exponential decay of non-Faradaic current (solid line) at an electrode in solution in response to a sudden change in the potential applied (dotted line) to the electrode.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a working electrode" includes a plurality of such working electrodes and equivalents thereof known to those skilled in the art, and so forth, and reference to "the working electrode" is a reference to one or more such working electrodes and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

In an electrochemical gas sensor, the gas to be measured typically passes from the surrounding atmosphere or environment into a sensor housing through a gas porous or gas permeable membrane to a first electrode or working electrode (sometimes called a sensing electrode) where a chemical reaction occurs. A complementary chemical reaction occurs at a second electrode known as a counter electrode (or an auxiliary electrode). The electrochemical sensor produces an analytical signal via the generation of a current arising directly from the oxidation or reduction of the analyte gas (that is, the gas to be detected) at the working electrode. A comprehensive discussion of electrochemical gas sensors is also provided in Cao, Z. and Stetter, J. R., "The Properties and Applications of Amperometric Gas Sensors," *Electroanalysis*, 4(3), 253 (1992), the disclosure of which is incorporated herein by reference.

The working and counter electrode combination produce an electrical signal that is (1) related to the concentration of the analyte gas and (2) sufficiently strong to provide a signal-to-noise ratio suitable to distinguish between concentration levels of the analyte gas over the entire range of interest. In other words, the current flow between the working electrode and the counter electrode must be measurably proportional to the concentration of the analyte gas over the concentration range of interest.

In addition to a working electrode and a counter electrode, an electrochemical sensor often includes a third electrode, commonly referred to as a reference electrode. A reference electrode is used to maintain the working electrode at a known voltage or potential. The reference electrode should be physically and chemically stable in the electrolyte.

Electrical connection between the working electrode and the counter electrode is maintained through the electrolyte. Functions of the electrolyte include: (1) to efficiently carry the ionic current; (2) to solubilize the analyte gas; (3) to support both the counter and the working electrode reactions; and (4) to form a stable reference potential with the reference electrode. Criteria for an electrolyte may, for example, include the following: (1) electrochemical inertness; (2) ionic conductivity; (3) chemical inertness; (4) temperature stability; (5) low cost; (6) low toxicity; (7) low flammability; and (8) appropriate viscosity.

In general, the electrodes of an electrochemical sensor provide a surface at which an oxidation or a reduction (a redox) reaction occurs to provide a mechanism whereby the ionic conduction of the electrolyte solution is coupled with the electron conduction of the electrode to provide a complete circuit for a current.

The measurable current arising from the sensor reactions within the electrochemical sensor is directly proportional to the extent of reaction occurring at the electrode. Preferably, therefore, a high reaction rate is maintained in the electrochemical sensor. For this reason, the counter electrode and/or the working electrode of the electrochemical sensor generally include an appropriate electrocatalyst on the surface thereof to support the reaction rate.

The gas diffusion electrode, which is typically the working electrode in sensors, provides for the confluence of the electrocatalyst of the gas diffusion electrode (usually a metal), the internal electrolyte of the sensor (usually a liquid solution), and the gas of interest (the analyte or target gas). This confluence is often referred to as the "triple point." To maximize the sensitivity of a sensor, efforts are made to maximize the number of triple points. Maximizing the number of triple points is commonly accomplished by using finely divided, high electrochemically accessible surface area catalytic metals, such as platinum (Pt) or iridium (Ir) "blacks." Descriptions of gas diffusion electrodes can be found in many references.

As gas diffusion electrodes commonly use high electrochemically accessible surface area metal particles, the actual or total usable electrochemically accessible surface area of the gas diffusion electrodes, and hence, electrical capacitance (see equation (2)), often far exceed their geometric area (for example, provided by $\pi r^2$ in the case of a circular electrode having a radius r). The electrochemically accessible surface area also typically varies greatly from sensor (electrode) type to sensor type. Table 1 sets forth electrical characteristics of typical gas diffusion electrodes used in a number of representative amperometric gas sensors wherein the geometric area of the electrodes was about $8 \times 10^{-4}$ $m^2$ (⅝" dia.).

TABLE 1

| Sensor Type | RMS noise, μA | AC impedance, Ω | Capacitance, F | Ratio of Total Electrochemically Accessible Surface to Geometric Surface Area |
| --- | --- | --- | --- | --- |
| CO | 0.689 | 4.48 | 0.3089 | 1415:1 |
| $H_2S$ | 8.847 | 4.53 | 0.2472 | 960:1 |
| $NO_2$ | 0.480 | 16.99 | 1.464 | 1100:1 |
| NO | 0.162 | 2.82 | $1.65 \times 10^{-2}$ | 27:1 |
| HCl | 0.124 | 2.72 | $1.32 \times 10^{-4}$ | 12:1 |

Table 1 sets forth characteristic data for several types of amperometric gas sensors, with the intended target gas listed in the first column. The RMS (root mean square) noise was calculated using baseline data (data taken when no target gas was present). The AC impedance was measured using a commercially available digital LCR meter. The total electrochemically active/accessible surface area was estimated using the cyclovoltammetric technique described in Tilak, B. V., Rader, C. G., & Rangarajan, R., *J. Electrochem. Soc.,* 124, (1977), 1879. This method involves performing cyclic voltammetric experiments on an electrode over a range of potentials where no Faradaic reactions occur. The scan rate of the cyclic voltammetric experiments is varied and a plot of resulting current vs. scan rate is directly related to the capacitance, and hence, the electrochemically accessible surface area of the electrode. However, there are other methods described in the literature that give similar results. Such methods can be applied to either rough or porous electrodes, as well as to smooth electrodes, for which the geometric area is a good approximation of the electrochemically active/accessible surface area.

It has been understood in the electrochemical sensor arts that pulsed potential techniques, as classically described, should be of no utility when applied to high electrochemically accessible surface area electrodes. This is particularly true when the very high double layer capacitances of typical gas diffusion electrodes are taken into account (see Table 1). Potential step experiments would appear to bear this out.

However, the present inventors have discovered that rough, high electrochemically accessible surface area, porous gas diffusion electrodes, similar to those detailed in Table 1, may be used in pulsed potential measurements using, for example, a rapid, large potential step. In a number of embodiments, amperometric gas sensors are operated at at least two different bias potentials to detect and measure one or more analytes (target gases). This methodology is, for example, illustrated in FIGS. 2A and 4.

The sensor may, for example, be operated by a potentiostat circuit that rapidly (for example, <1 sec) switches the working electrode between the two bias potentials. The sensor current may, for example, be sampled at the first potential shortly before the working electrode is switched to the second potential. The output signal may, for example, be sampled and deconvoluted after at least 95%, after at least 99% or after more than 99% of a time period for alternating between the first potential and the second potential has past. In general, the amount of time between sampling the output signal and switching to the potential may, for example, be minimized to a limit determined by the sensor electronics. Deconvolution of the sensor signal is possible because the Faradaic and non-Faradaic contributions to the overall current behave differently with regard to time. As discussed earlier, the non-Faradaic current decays exponentially with time following the potential change. The Faradaic current rapidly reaches a steady-state value that is equal to the diffusion limited value for the same sensor operated at a single potential. Deconvolution, at its simplest level, involves sampling the total current at some fixed, finite time following the potential change. The longer one waits to sample the output signal, the greater the decay in the non-faradaic portion of the signal. Current theory and understanding in the art holds that, because of relative magnitudes of the Faradaic and non-Faradaic currents and variation in the non-Faradaic current from pulse to pulse (particularly with short pulses), it is not possible to detect the small Faradaic current in the presence of a much larger and variable non-Faradaic current. However, the present inventors have discovered that a non-Faradaic baseline current (determined, for example, in the absence of a reactive/analyte gas for a particular potential change/signal measurement sequence) may be subtracted from an output signal including both a Faradaic and a non-Faradaic components to determine the Faradaic component.

At the first potential, at least a first intended target gas is electrochemically oxidized or reduced (a redox reaction). At the second potential, the electrocatalyst of the working electrode is substantially inactive or inactive to catalyze a redox reaction of the first target gas. Even in the case that a sensor hereof is operated to detect the concentration of only a single target gas, there are advantages to operating the sensor in a manner in which the working electrode potential is varied, alternated or pulsed between a potential at which a redox reaction of the target gas occurs and a potential at which no or substantially no redox reaction of the target gas occurs. For example, if the chemistry of the sensor is complicated by one or more complimentary or interfering reactions, it may be beneficial to change the potential of the working electrode to a potential at which the primary reaction and such complimentary reactions do not occur. Having the potential of the working electrode in a range in which no reactions or substantially no reactions occur for a substantial amount or most of the sensor lifetime can uncomplicate the chemistry of the sensor and may extend sensor lifetime.

For instance, some sensors include an auxiliary reagent or species in solution to promote the analytical reaction used in sensing a target gas. If the auxiliary reagent also undergoes electrochemical reaction at the same potential of the target gas, it may be beneficial to pulse the working electrode from a potential where the target gas and the auxiliary reagent are both substantially inactive to preserve the supply of the auxiliary reagent. Symbolically, for target gas A, and auxiliary reagent B, A and B react to form an electrochemically labile complex or compound AB, which undergoes reduction at a given applied potential, $pot_2$:

$$A+B \rightarrow AB \qquad \text{eq. (5)}$$

$$AB + ne^- \rightarrow AB^- \text{ (sensing reaction), } pot_2 \qquad \text{eq. (6)}$$

The sensing reaction is the reduction of the complex or compound, AB (equation (6)). However, the auxiliary reagent also undergoes reduction at potential $pot_2$, according to:

$$B + ne^- \rightarrow B^-, \qquad \text{eq. (7)}$$

but is substantially inactive at some other potential, $pot_1$. Therefore, maintaining the electrode for at least some time at $pot_1$ maintains and maximizes the availability of B for participation in the reaction set forth in equation (5).

A similar situation may occur with respect to the condition of the working electrode. Metallic electrodes (and some non-metallic electrodes such as carbon) attain differing surface oxide states at different applied potentials. These differing oxide states may affect the electrocatalytic properties of the electrode. Maintaining an electrode at one potential, $pot_1$, can maintain the electrode in a physical state that promotes the desired electrocatalytic reaction even though that reaction occurs at a different applied potential, $pot_2$, wherein that desired electrode state is not favored. Pulsing the electrode between $pot_1$ and $pot_2$ can maximize the activity of the electrode for the desired electrochemical reaction as compared to the case in which the electrode is maintained only at $pot_2$.

In general, the phrase "substantially inactive" when used in connection with an electrode for a particular reaction and potential as used herein refers to a potential which is more positive than the appearance potential for a reduction reaction and more negative than an appearance potential for an oxidation reaction. The concept of an appearance potential is further described below.

In that regard, electrochemical techniques provide a method of "tuning" or adjusting the catalytic power or energy of a catalytic surface (the electrode surface). Most modern electrochemical techniques assume the presence of a reference electrode. As described above, a reference electrode is an electrode having a thermodynamic potential fixed by it structure, against which the potential of the working electrode is measured or controlled. By driving the potential of the working electrode negatively (cathodically) with respect to a reference electrode, a potential will be reached where species in solution will undergo reduction (that is, an algebraic decrease in the oxidation number). Prior to reaching a certain, critical cathodic potential, no reduction occurs, essentially no current flows through the cell, and the electrode may be said to be "substantially inactive" with regard to the reduction of the dissolved species.

Conversely, the working electrode can be driven positively, with respect to the reference electrode, until a potential is reached where a dissolved species can undergo oxidation (that is, an algebraic increase in the oxidation number). Once again, until a certain, critical anodic potential is reached, the dissolved species does not undergo oxidation, and the working electrode can be said to be "substantially inactive" with regard to the oxidation of the dissolved species.

Figure 1B:
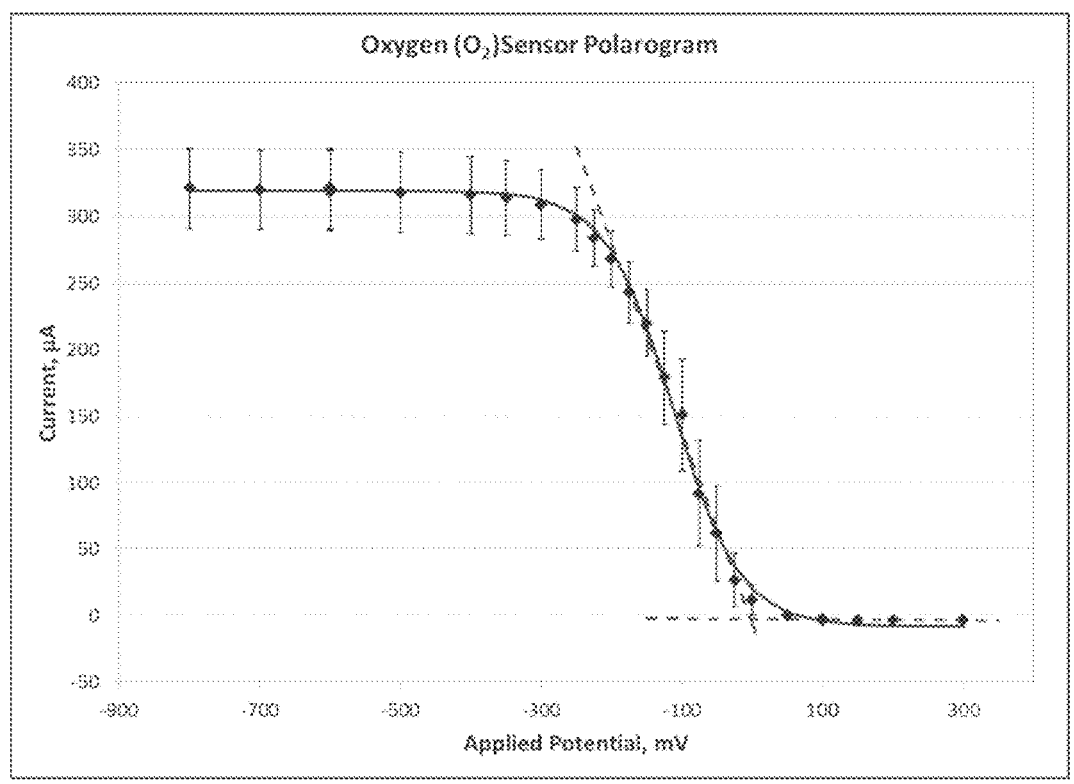
FIG. 1B illustrates a polarogram (a plot of current vs. applied potential) for the reduction of oxygen in acidic aqueous solution and the determination of an appearance potential.

For example, FIG. 1B illustrates a polarogram (a plot of current vs. applied potential) for the reduction of oxygen in acidic aqueous solution. At potentials more negative than about −400 mV, the reduction of oxygen proceeds readily. The typical operating bias of oxygen sensors is between −400 and −800 mV. This is at the top of the polarographic "wave," and the current at these potentials is said to be "diffusion limited" (that is, limited by the rate of diffusion of oxygen to the working electrode of the sensor). At potentials more positive than about +50 mV, no current flows (because there is no reduction of oxygen as such potentials). Electrochemists use the term "appearance potential" to designate the approximate potential at which the polarographic wave begins. It is commonly found by determining the intersection of the two straight dashed lines in the figure. These lines were the result of linear regression analysis of the data between about 0 and −400 mV (the "wave" or rising portion of the curve) and between about 0 and +350 mV (the "baseline" portion of the curve). In the case of the data shown in FIG. 1B, the appearance potential is about −2 mV. Therefore, the working electrode can be said to be substantially inactive for the reduction of oxygen at any potential more positive than about −2 mV, and becoming even more inactive at more positive potentials.

The previous discussion was presented in connection with a reduction reaction, and more particularly, the reduction of oxygen. However, a similar discussion applies in the case of oxidation reactions and the working electrode can be said to be substantially inactive for a given oxidation reaction at potentials more negative than the appearance potential for that oxidation reaction.

In a number of embodiments, the electrocatalyst of the working electrode may be active to catalyze a redox reaction of a second target gas at a second potential. At the first potential, the electrocatalyst is substantially inactive or (completely) inactive to catalyze a redox reaction of the second target gas. In this way, one sensor may be used to measure at least two different target gases.

In addition to having a small total electrochemically accessible surface area, it has been understood in the electrochemical arts that any potential pulse should be small (for example, less than about $0.059/n$ volts (at 25° C.), where n is the number of electrons transferred in the electrochemical reaction). However, the present inventors have discovered that the magnitude of the potential change or pulse in the present sensor may be significantly greater (for example, two times that amount ($0.18/n$ volts), ten times that amount ($0.59/n$ volts) or even twenty times that amount ($1.18/n$ volts) at 25° C.).

It has also been understood in the electrochemical arts that the time between pulses should be long to allow the charging current to decay to small values. However, the time period between changes in working electrode potential in the sensors hereof may be less than 5 seconds. In a number of embodiments, the time period for alternating between the first potential and the second potential is no more than 1 second, no more than 500 milliseconds, no more than 100 milliseconds or even no more than 50 milliseconds. In general, quickly alternating or pulsing the potential of the working electrode may provide for relatively quick response to changes in concentration of a target gas or target gases in the environment.

Figure 2A:
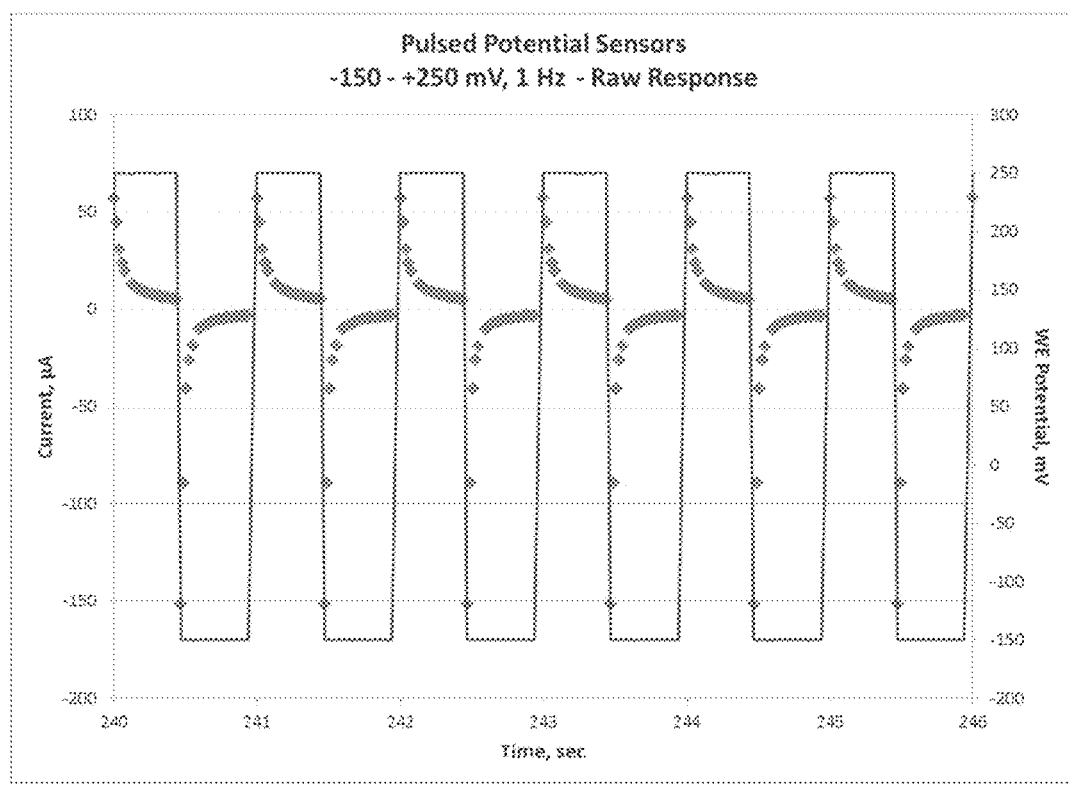
FIG. 2A illustrates pulsed operation of a high electrochemically accessible surface area, rough gold (Au) working electrode in an acidic electrolyte.
Figure 2B:
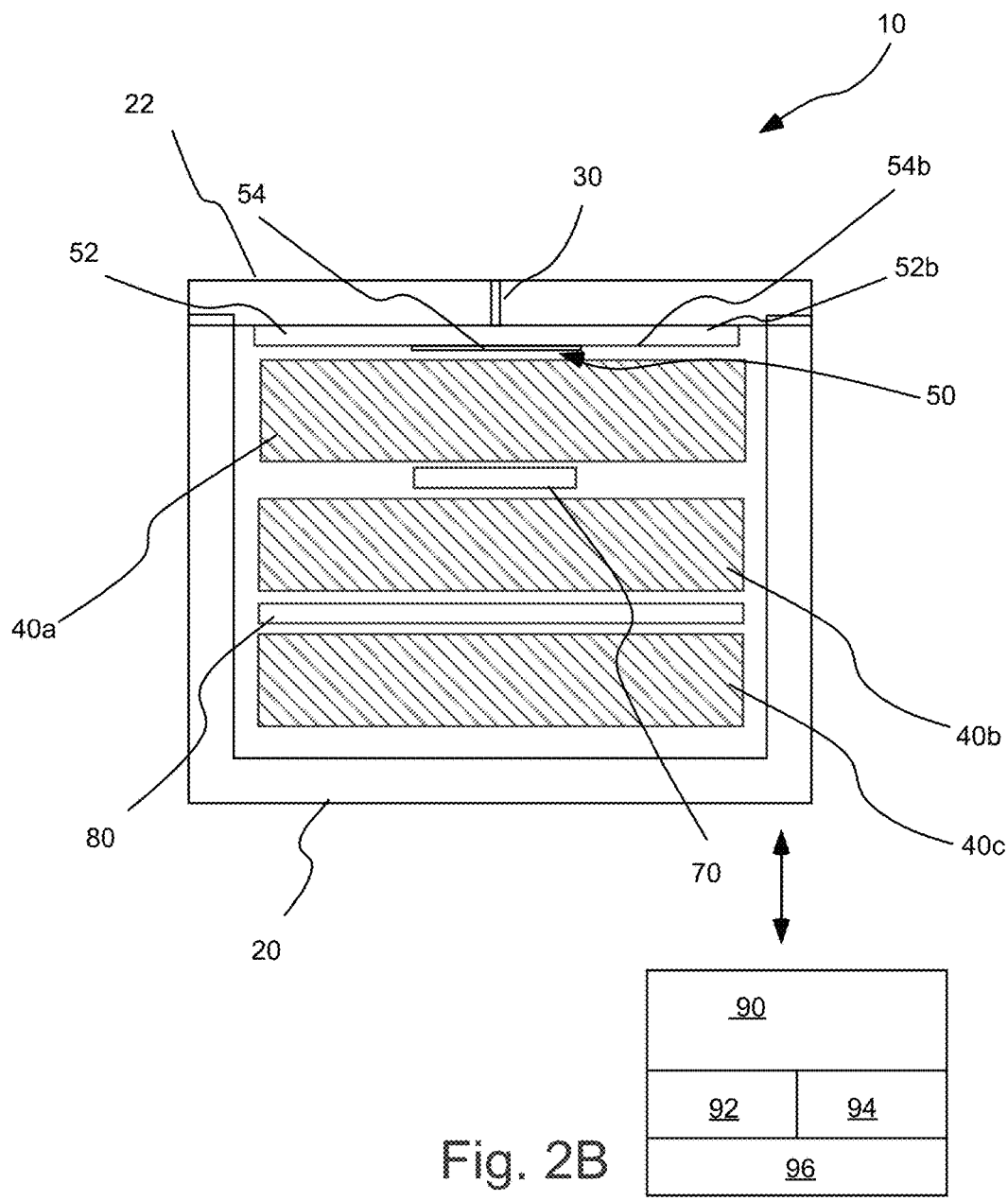
FIG. 2B illustrates schematically an embodiment of a sensor hereof.

FIG. 2B illustrates a schematic diagram of a representative embodiment of an electrochemical sensor 10 used in the studies hereof. Sensor 10 includes a housing 20 having a gas inlet 30 for entry of one or more target gases or analyte gases into sensor 10. In the illustrated embodiment, electrolyte saturated wick materials 40a, 40b and 40c separate a working electrode 50 from a reference electrode 70 and a counter electrode 80 within sensor 10 and/or provide ionic conduction therebetween via the electrolyte absorbed therein. Electronic circuitry 90 as known in the art is provided, for example, to maintain a desired potential difference between working electrode 50 and reference electrode 70, to vary or pulse the potential difference as described herein, and to process an output signal from sensor 10. Electronic circuitry 90 may, for example, include or be in operative connection with a processor system 92 (including, for example, one or more processors such as microprocessors) and a memory system 94.

One or more algorithms for control of sensor 10 and processing of data may, for example, be stored in memory system 94, which is in operative connection with processor system 92. Such algorithms may, for example, include an algorithm for determining a non-faradaic baseline for a potential change sequence and deconvoluting an output signal by subtracting the non-faradaic baseline from the total output signal to determine the faradaic component of the output signal as described above. The non-faradaic baseline corresponds to the sensor output for a given potential change/variation protocol in the absence of a redox reaction of, for example, the analyte or a simulant therefor. Output of sensor 10 may, for example, be provided to a user or users via a user interface 96 (see, for example, FIG. 2B; for example, including a display) in operative connection with processor system 92.

In the illustrated embodiment, working electrode 50 may be formed by, for example, depositing a first layer of catalyst 54 on a first diffusion membrane 52 (using, for example, catalyst deposition techniques known in the sensor arts). Working electrode 50 may be attached (for example, via heat sealing) to an inner surface of a top, cap or lid 22 of housing 20.

FIG. 2A shows the current (♦) (plotted against the left vertical axis) that results from the application of a potential pulse program applied to a relatively high electrochemically accessible surface area gold (Au) working or sensing electrode in an acidic electrolyte. The pulse program applied to the working electrode is shown in the solid line and is plotted against the right vertical axis. The pulse program switched the potential (solid line) applied to the working electrode from −150 mV to +250 mV (vs an internal platinum/air (Pt|air) pseudo reference electrode) every 500 msec. The spiking and decay behavior illustrated in FIG. 1A is clearly evident in FIG. 2A.

Figure 3:
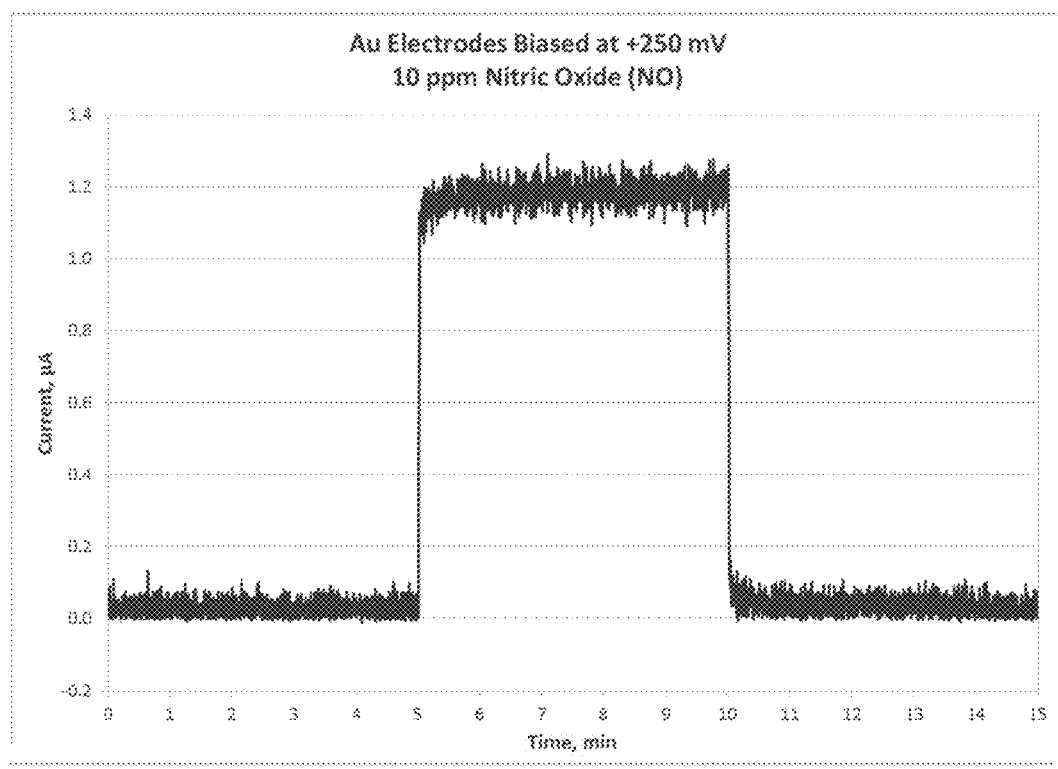
FIG. 3 illustrates the current resulting from the application of 10 ppm nitric oxide (NO) to a high electrochemically accessible surface area Au working electrode biased at +250 mV vs. a Pt|air reference electrode.

In typical usage, fuel cell-type amperometric electrochemical gas sensors are operated at a constant DC bias potential to avoid the deleterious effects of charging currents, and to have a constant, stable, near-zero baseline (background current when no target or analyte gas is present). FIG. 3 illustrates an example of the typical operation of an electrochemical gas sensor. In that regard, FIG. 3 illustrates the current signal that results from the application of 10 parts-per-million (ppm) nitric oxide to a high surface Au working electrode, in an acidic electrolyte. The Au electrode was biased at a constant +250 mV vs. an internal Pt|air reference electrode. The analyte gas (NO) was applied at the five (5) minute mark and was removed at 10 minutes.

In the sensor configuration of FIG. 3, a gold working electrode in an acidic electrolyte, biased at +250 mV, is operable for detecting nitric oxide. The sensor has a low, flat baseline, a rapid response, and high sensitivity to the target gas. The sensor response is a result of the rapid and efficient oxidation of nitric oxide to nitrogen dioxide according to:

$$2NO + O_2 \rightarrow 2NO_2. \tag{8}$$

Figure 4:
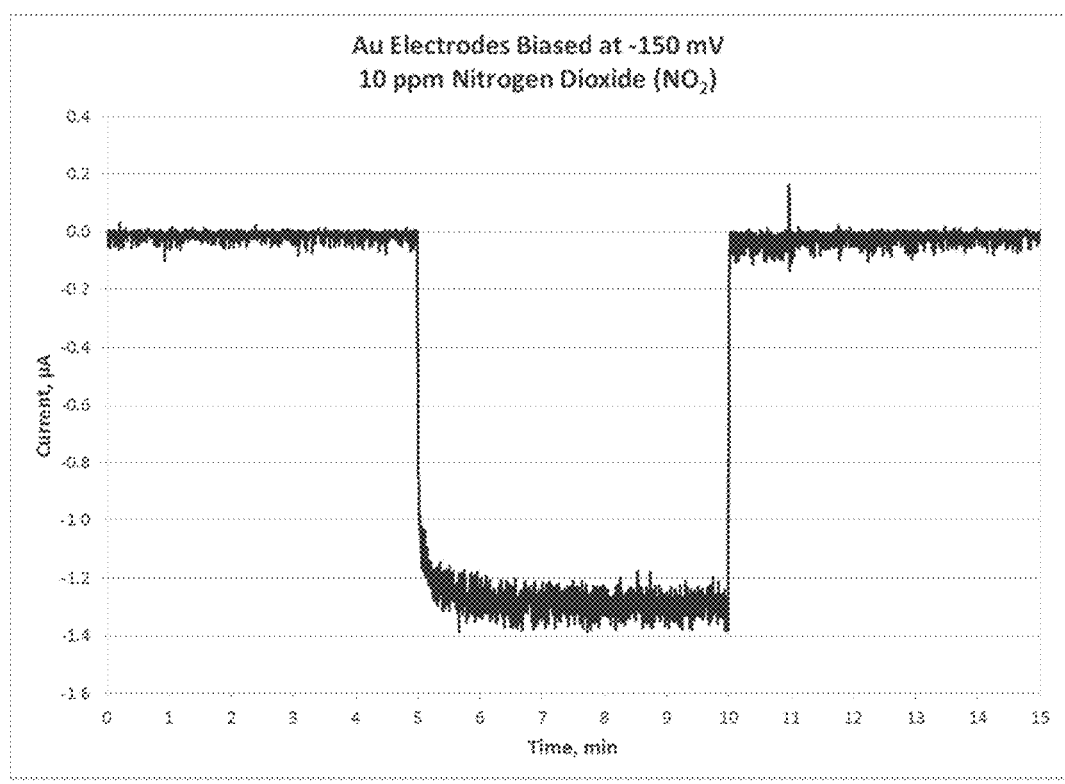
FIG. 4 illustrates the current resulting from the application of 10 ppm nitrogen dioxide ($NO_2$) to a high electrochemically accessible surface area Au working electrode biased at −150 mV vs. a Pt|air reference electrode.

However, the same sensor configuration, when operated at a different bias potential may be used for sensing a different analyte gas without interference from the application of NO. FIG. 4, for example, illustrates the current signal obtained when the same sensor is biased at −150 mV (vs. Pt|air) and challenged with nitrogen dioxide. Thus, in the same arrangement (that is, a high electrochemically accessible surface area Au working electrode in an acidic electrolyte) but under a different potential, the electrochemical sensor functions as a very efficient sensor for detecting nitrogen dioxide. Nitrogen dioxide is reduced to nitric oxide according to:

$$2NO_2 \rightarrow O_2 + 2NO. \tag{9}$$

In industrial hygiene applications, it is often desirable to detect and measure both nitrogen dioxide and nitric oxide. This functionality is, for example, particularly desirable in underground mining applications wherein diesel engines are used. One way to accomplish this goal is to produce a gas detection instrument with both a nitric oxide sensor and a nitrogen dioxide sensor. However, from the above discussions it is clear that the same amperometric sensor may be used for either or both gases, with the only difference being the bias potential applied to the working electrode. In a number of embodiments hereof, two gases, such as nitrogen dioxide and nitric oxide, may be monitored using one sensor by rapidly switching between two bias potentials.

Figure 5:
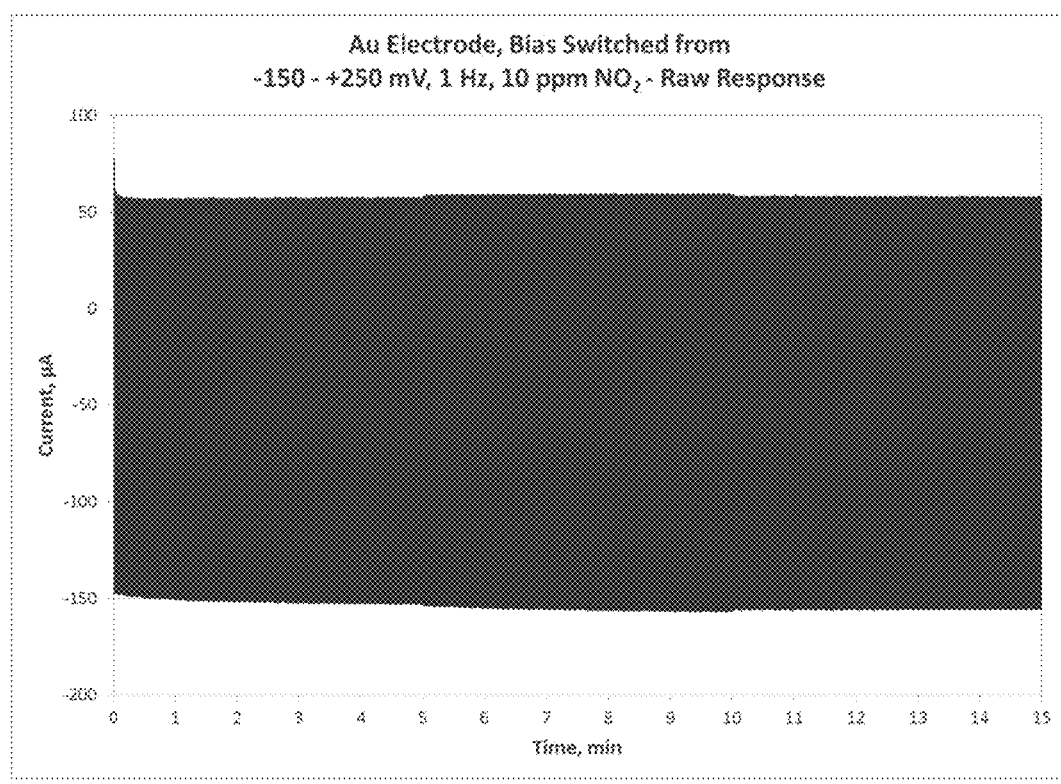
FIG. 5 illustrates the current resulting from the application of a rapidly switched bias potential (−150 mV to 250 mV vs. Pt|air, 1 Hz) to a high electrochemically accessible surface area gold working electrode, onto which is superimposed the current resulting from the reduction of 10 ppm nitrogen dioxide at −150 mV, wherein the nitrogen dioxide was applied at a flow rate of 250 mL/min and was commenced at the five (5) minute mark and ended at ten minutes.
Figure 6:
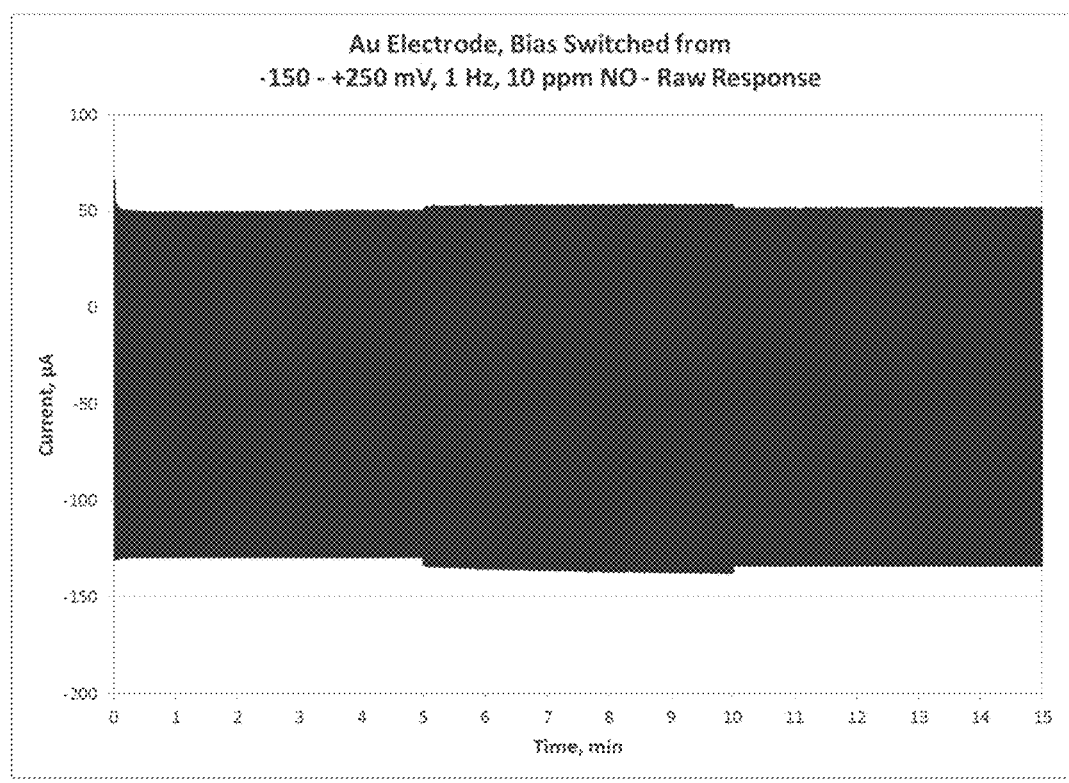
FIG. 6 illustrates the current resulting from the application of a rapidly switched bias potential (−150 mV to 250 mV vs. Pt|air, 1 Hz) to a high electrochemically accessible surface area gold working electrode, onto which is superimposed the current resulting from the oxidation of 10 ppm nitric oxide at +250 mV, wherein the nitric oxide was applied at a flow rate of 250 mL/min and was commenced at the five (5) minute mark and ended at ten minutes.

FIGS. 5 and 6, illustrate, respectively, the application of 10 ppm nitrogen dioxide and 10 ppm nitric dioxide to a sensor with a high electrochemically accessible surface area Au working electrode wherein the bias potential is rapidly (once per second) switched from −150 mV to 250 mV (vs. the internal Pt|air reference electrode). In each case, the test gas, either nitrogen dioxide or nitric oxide was applied at ten (10) minutes in the graph and removed at fifteen (15) minutes. The flow rate in each case was 250 mL/min. FIGS. 5 and 6, while they are complimentary experiments, contain very little useful information. The overall current displacement from the application of either test gas in very small, compared to the background current, and it is virtually impossible to tell which analyte is being applied to the sensor.

However, if the current is sampled just before the potential is switched, contrary to theory and expectations, much more useful analytical information is obtained. FIGS. 7 through 10 illustrates the results of such experiments.

Figure 7:
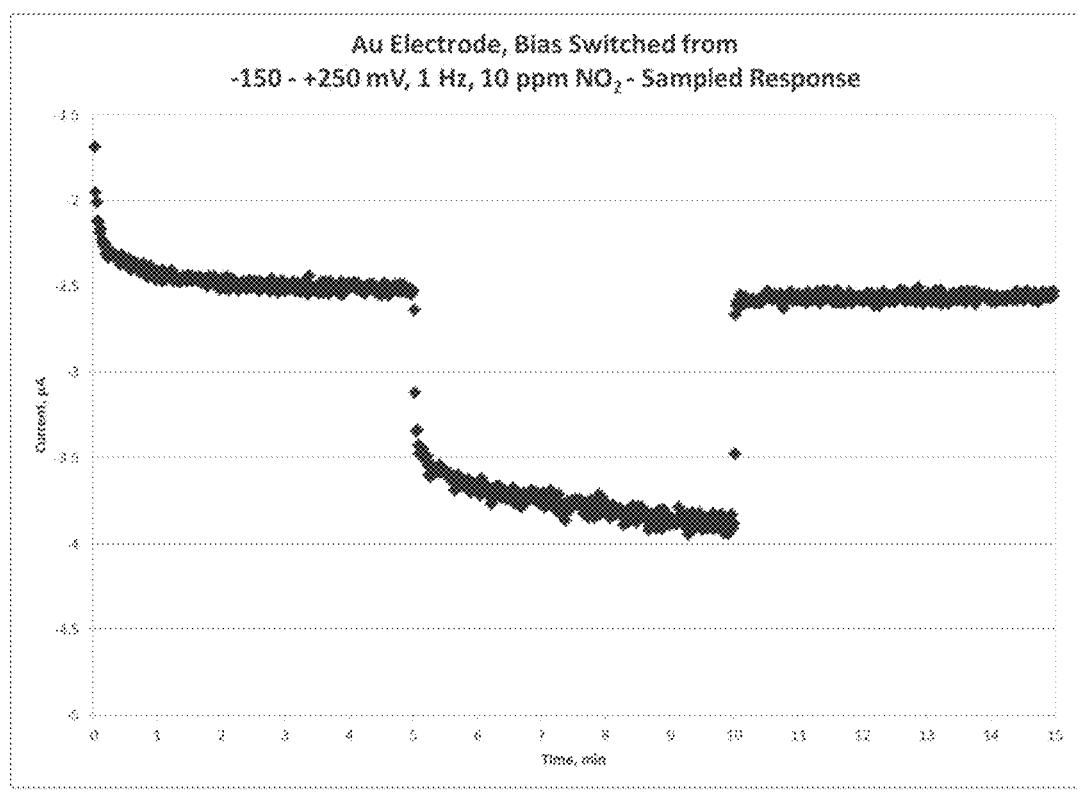
FIG. 7 illustrates an experimental trace resulting from a current sampled pulsed potential experiment involving the reduction of nitrogen dioxide on a high electrochemically accessible surface area Au electrode at −150 mV vs. Pt|air, wherein the residual baseline is of the same order of magnitude as the analytical signal.

In that regard, FIG. 7 illustrates the experimental result of applying a potential pulse program to a high electrochemically accessible surface area Au working electrode. The potential of the electrode was pulsed between −150 and +250 mV vs. an internal Pt|air reference electrode, as described in FIG. 1 and the accompanying discussion. In contrast to the data illustrated in FIG. 5, which is essentially the same experiment, in this case the current present at the working electrode was sampled at an applied potential of −150 mV, immediately before the applied potential was switched to +250 mV. Referring to FIG. 2A, this current sampling was accomplished immediately prior to the 241, 242, 243 second marks, and so on. According to FIGS. 2A, 5, and 7, even though the non-Faradaic charging current decayed somewhat, it was still substantial with regard to the analytical Faradaic current resulting from the application of 10 ppm nitrogen dioxide to the working electrode.

Figure 8:
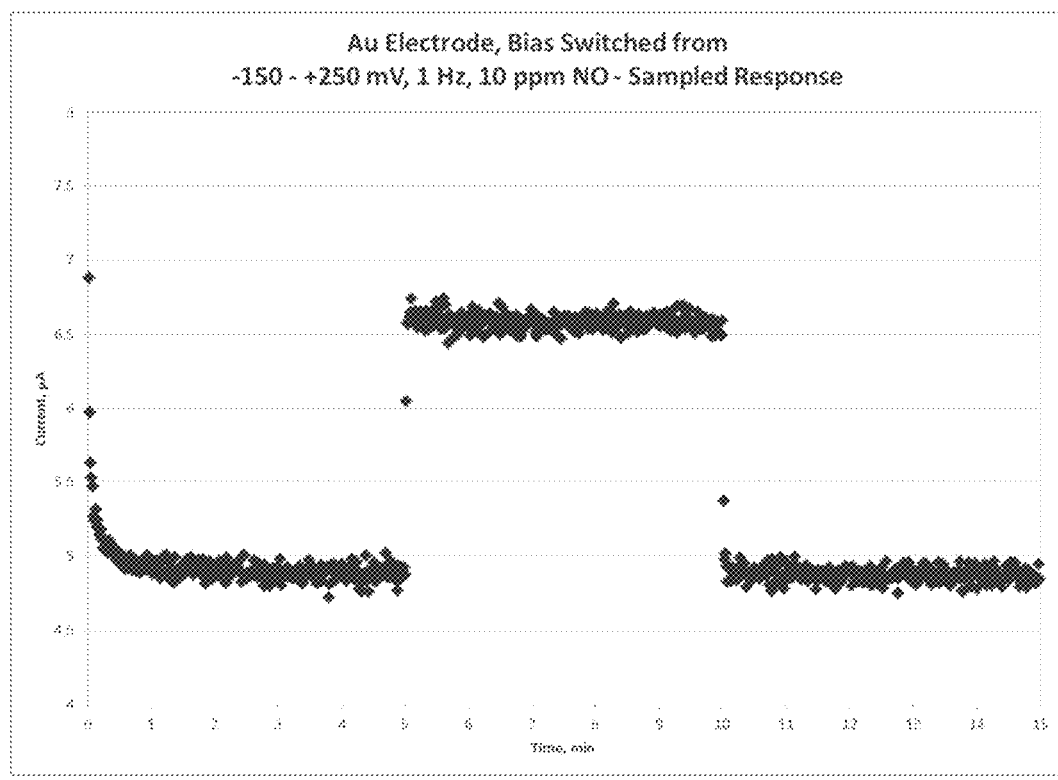
FIG. 8 illustrates an experimental trace resulting from a current sampled pulsed potential experiment involving the oxidation of nitric oxide on a high electrochemically accessible surface area gold (Au) electrode at +250 mV vs. Pt|air, wherein the residual baseline is of the same order of magnitude as the analytical signal.

FIG. 8 shows the results of the complimentary experiment involving the oxidation of nitric oxide at +250 mV (see also FIGS. 2A and 6). In the case of FIG. 8, the current was sampled at +250 mV, immediately prior to switching the applied potential to −150 mV, that is, at the 240.5, 241.5, 242.5, etc. (see FIG. 2A) points in the experiment. Again, the non-Faradaic currents were substantial with regard to the analytical Faradaic currents, which is exactly the opposite of that normally required for the successful pulsed operation of analytical electrodes.

Figure 9:
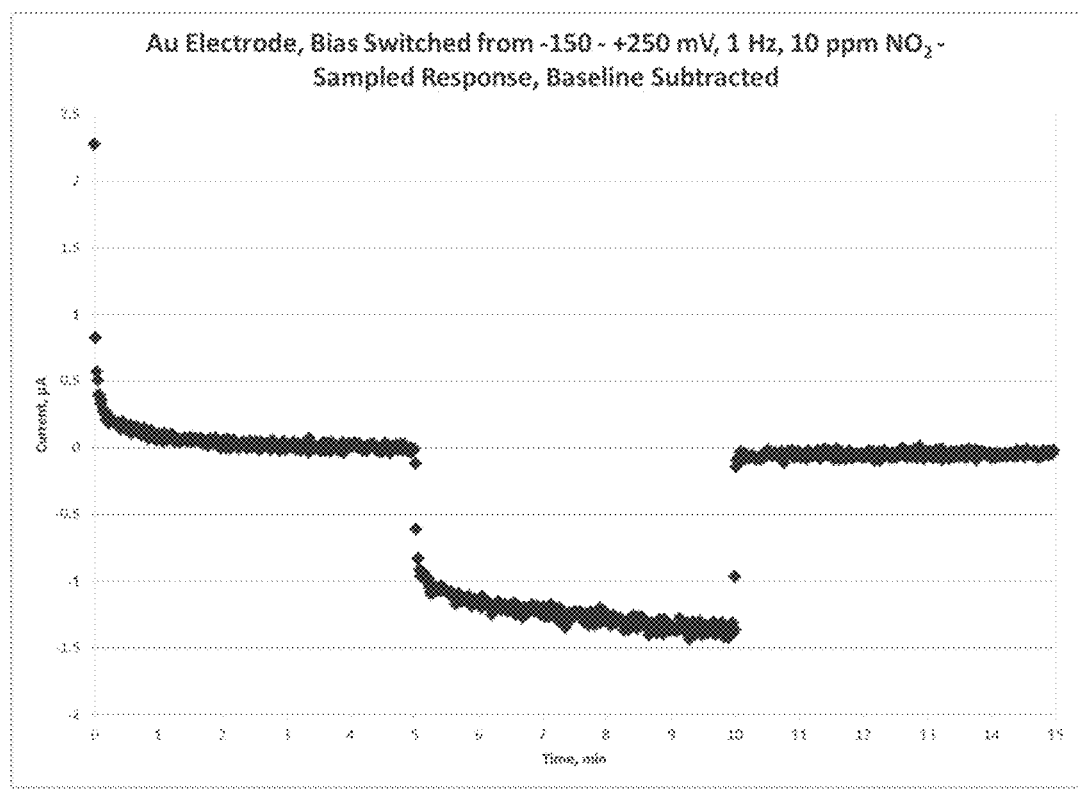
FIG. 9 illustrates the data of FIG. 7 with the non-Faradaic baseline current subtracted.
Figure 10:
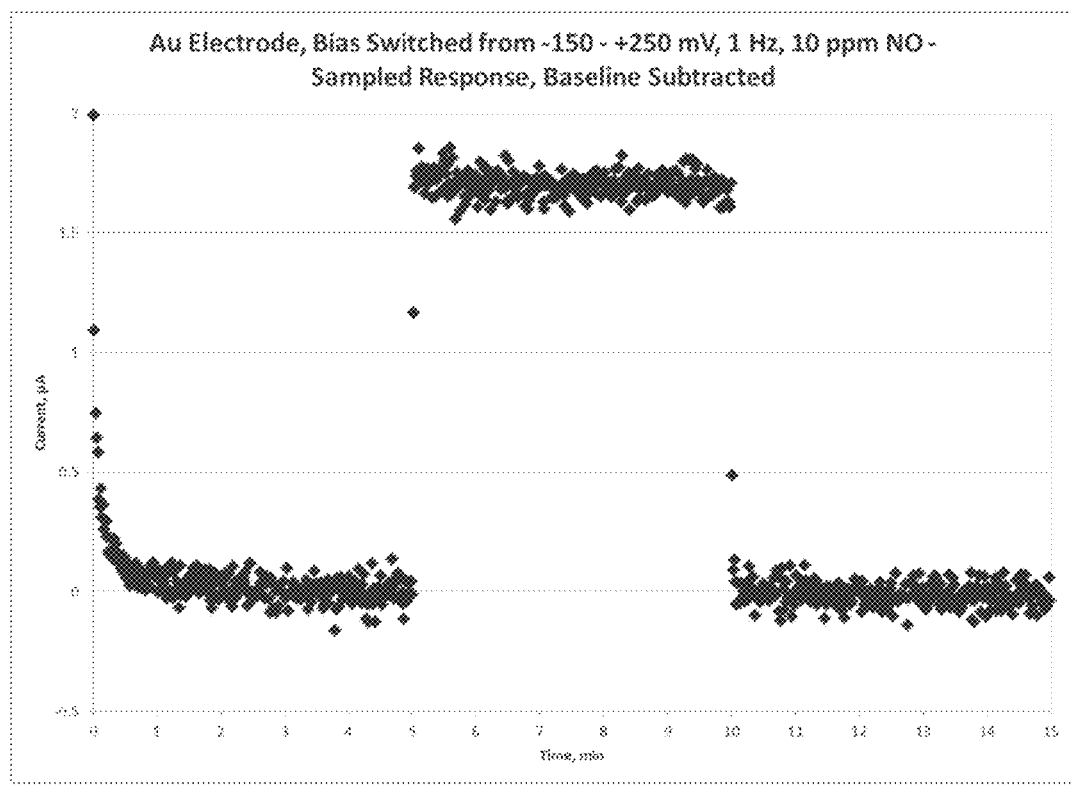
FIG. 10 illustrates the data of FIG. 8 with the non-Faradaic baseline current subtracted.

FIGS. 9 and 10 show that with simple de-convolution, pulsed operation of high electrochemically accessible surface area electrodes resulted in a very useful and efficient gas detection apparatus for the simultaneous detection of nitrogen dioxide and nitric dioxide. FIGS. 9 and 10 depict the data of FIGS. 7 and 8 with the non-Faradaic "baseline" current subtracted from the overall trace, demonstrating performance on a par with DC operation (FIGS. 3 and 4). In both cases, the non-Faradaic current between minutes 4 and 5 was averaged and subtracted from each point in the Figures.

Figure 11:
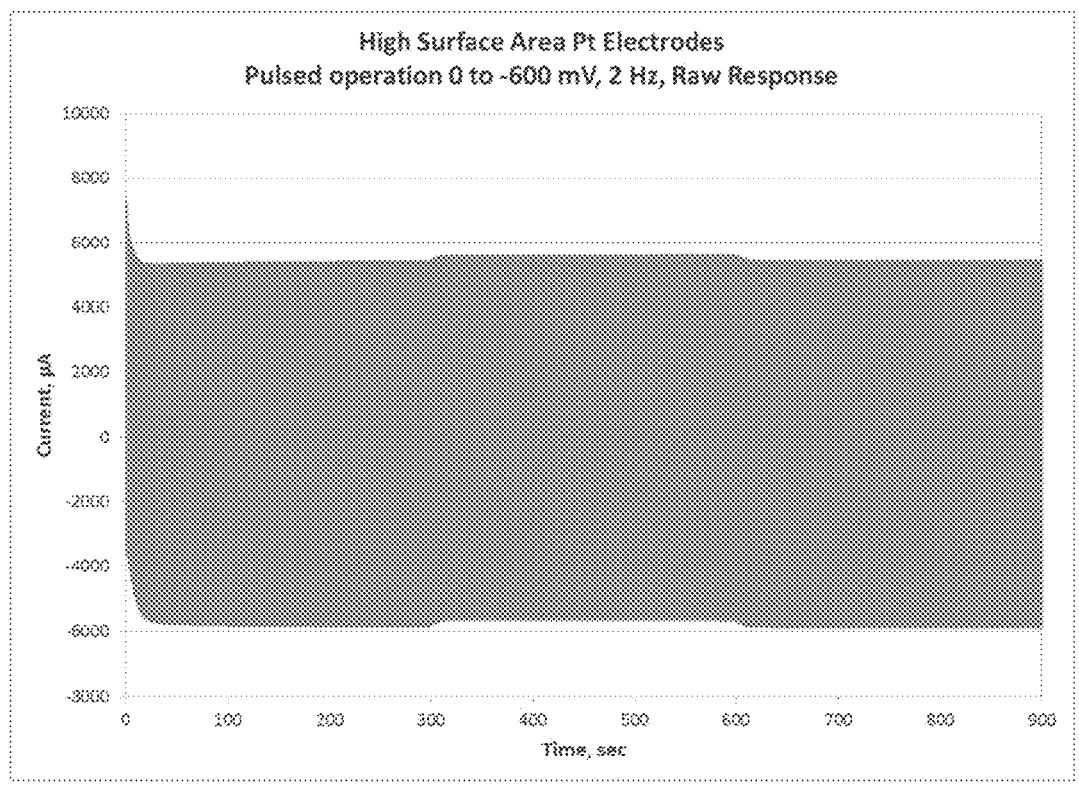
FIG. 11 illustrates the current resulting from a rapidly switched bias potential (0 to −600 mV vs. Pt|air, 1 Hz) applied to a high electrochemically accessible surface area platinum (Pt) electrode in air (20.8 vol-% oxygen, balance nitrogen) onto which is superimposed the current resulting from the application of nitrogen.

FIGS. 11 through 14 show the same type of rapid potential program applied to a high electrochemically accessible surface area platinum (Pt) electrode (see Table 1) immersed in a strong mineral acid electrolyte. Such a sensor may, for example, be used for oxygen sensing. A potential program was applied to this electrode consisting of immediate steps from 0 to −600 mV (vs. an internal Pt|air reference electrode). The potential program was applied at a frequency of 1 Hz. FIG. 11 is the raw current response as a result of the application of this pulse program. The sensor under discussion was an oxygen sensor and it was exposed to air (20.8 vol-% oxygen). In the experiment, nitrogen was applied to the sensor at the five (5) minutes in the graph and air was re-applied at 10 minutes. The flow rate of both air and nitrogen was 250 mL/min. The algebraic decrease in current (oxygen is reduced in this type of sensor, resulting in negative currents) is barely apparent in FIG. 11.

Figure 12:
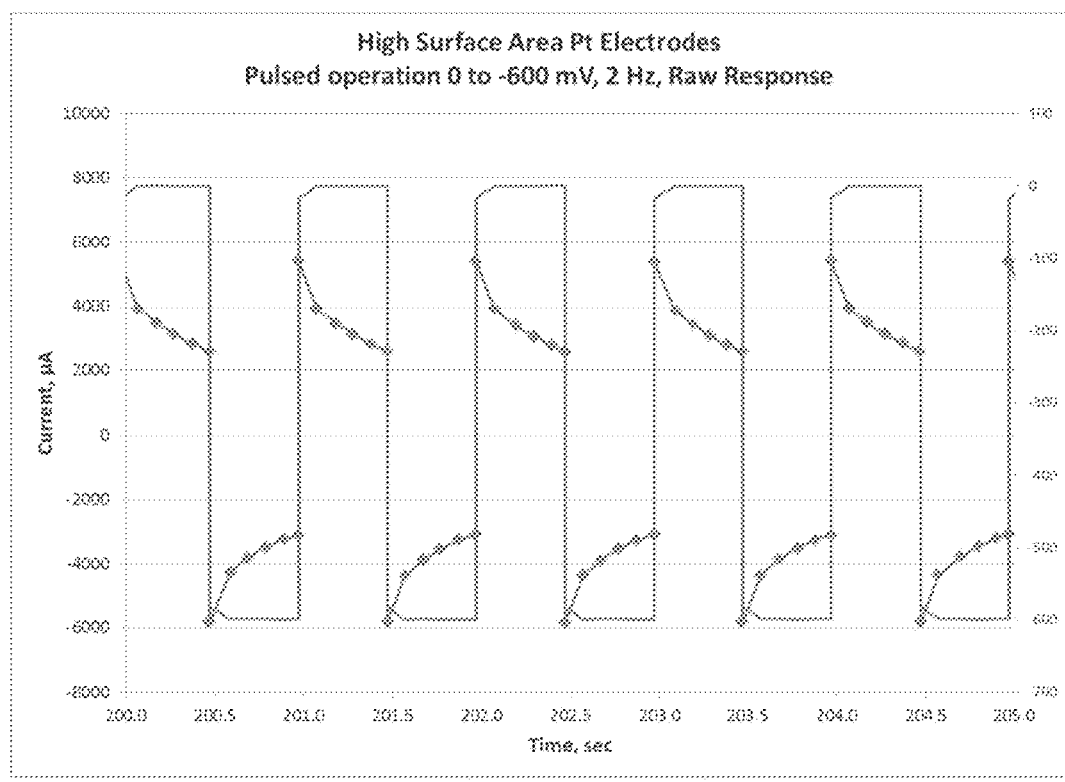
FIG. 12 illustrates pulsed operation of a high electrochemically accessible surface area, rough platinum (Pt) working electrode in an acidic electrolyte.

FIG. 12 illustrate an expanded scale version of a small portion of the experiment of FIG. 11, showing the application of the potential program and the resulting current. This portion of the trace includes a time period when the sensor was exposed to oxygen. The programmed potential pulse applied to the working electrode is shown in the solid line and plotted against the right vertical axis. As described above, the applied potential was switched between 0 and −600 mV vs. an internal Pt|air reference electrode. The resulting current profile (♦) is plotted against the left hand vertical axis.

Figure 13:
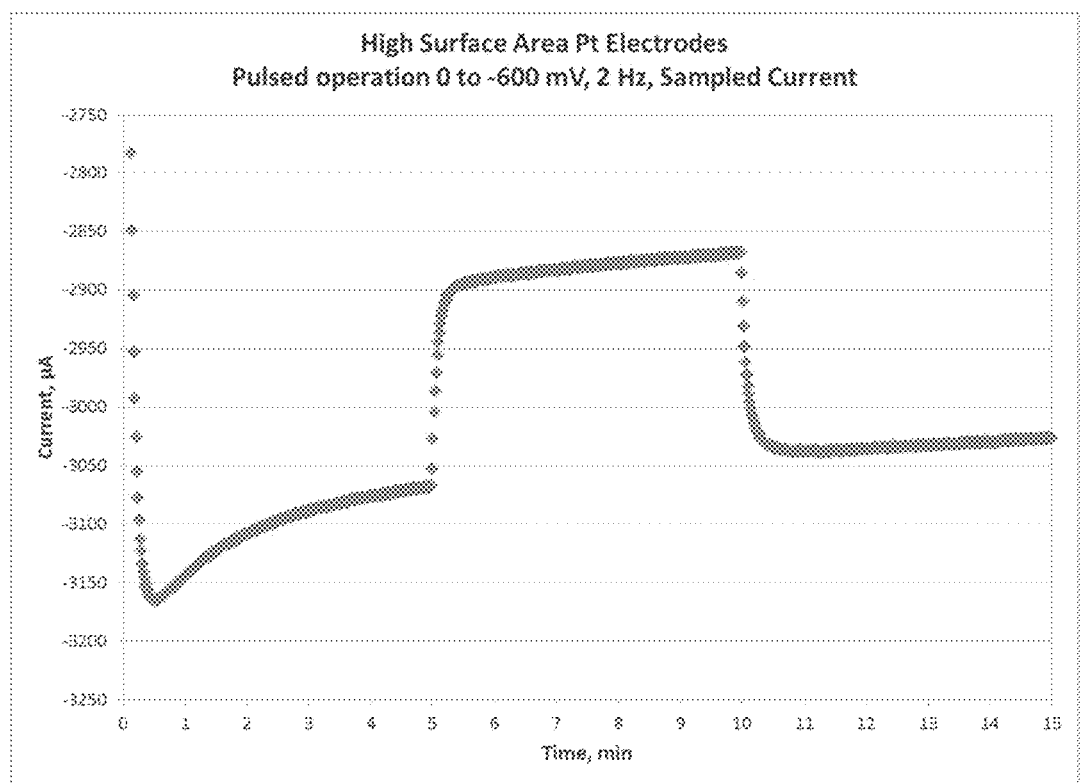
FIG. 13 illustrates the sampled current profile of the data depicted in FIGS. 10 and 11.
Figure 14:
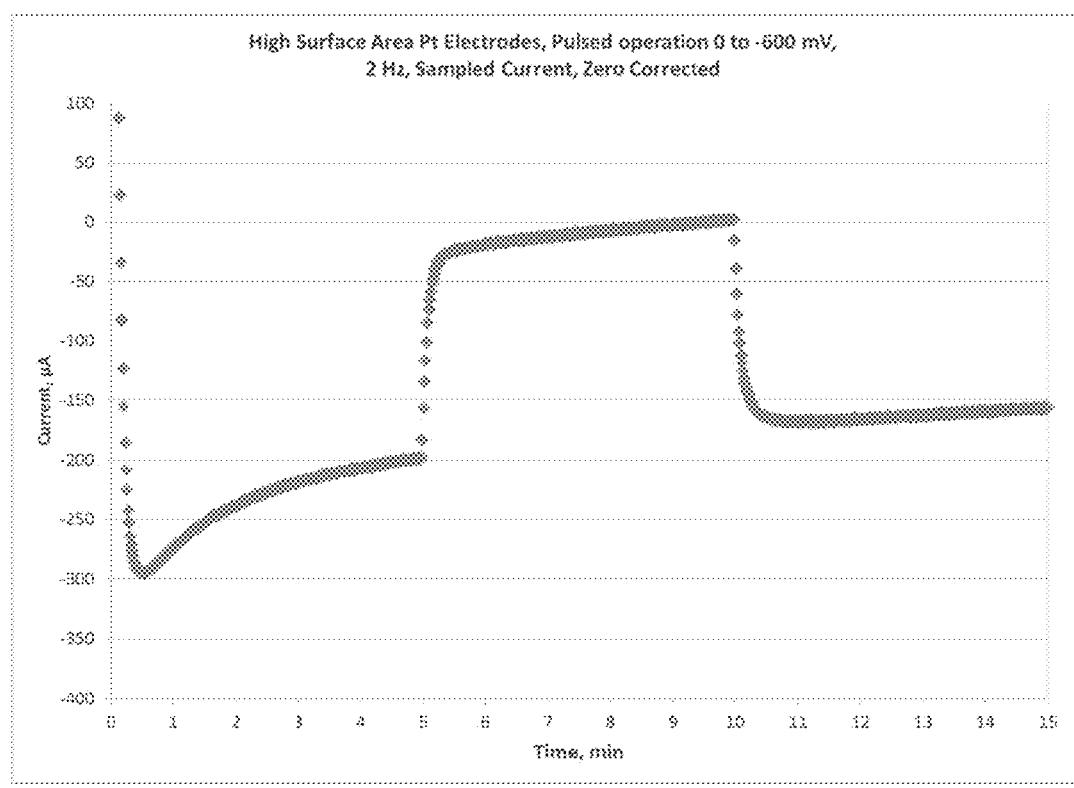
FIG. 14 illustrates the data of FIG. 13 with the non-Faradaic baseline current subtracted.

FIG. 13 is a sampled current presentation of the data shown in FIGS. 11 and 12. In this case, the current was sampled at −600 mV, immediately before the potential was switched to 0 mV. Referring to FIG. 12, this would be data sampled at time 200.0 sec, 201.0, sec, and so on. The signal decrease resulting from the application of nitrogen is clearly seen. Once again, oxygen is being reduced at −600 mV, resulting in negative current, with the application of nitrogen between five (5) and ten (10) minutes resulting in a positive excursion of the current signal. FIG. 14 is the same current profile with the non-Faradaic nitrogen baseline current subtracted out. This was accomplished by taking an average value of the current observed toward the end of the application of pure nitrogen, that is, between times 9.5 and 10 minutes, and subtracting that average value from each data point shown in FIG. 13.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of operating an electrochemical gas sensor comprising at least one working electrode comprising an electrocatalyst and having a ratio of total electrochemically accessible surface area to geometrical surface area of at least 2:1, comprising:
    alternatively biasing a potential of the working electrode to a first potential at which the electrocatalyst is active to catalyze a redox reaction of a first target gas and to a second potential, different from the first potential, at which the electrocatalyst is substantially inactive to catalyze the redox reaction of the first target gas, a plurality of times,
    measuring a first output signal arising from the redox reaction of the first target gas at the first potential; and
    deconvoluting the first output signal while the working electrode is biased at the first potential to separate a portion of the first output signal arising from non-faradaic current to determine a concentration of the first target gas.

2. The method of claim 1 further comprising deconvoluting the first output signal while the at least one working electrode is biased at the first potential to separate the portion of the first output signal arising from non-faradaic current to determine a concentration of the first target gas each of the plurality of times the potential of the at least one working electrode is biased to the first potential.

3. The method of claim 2 wherein the ratio of total electrochemically accessible surface area to geometrical surface area is at least 10:1.

4. The method of claim 2 wherein the ratio of total electrochemically accessible surface area to geometrical surface area is at least 200:1.

5. The method of claim 3 wherein the first output signal is deconvoluted after at least 95% of a time period for alternating between the first potential and the second potential is past.

6. The method of claim 3 wherein the first output signal is deconvoluted after at least 99% of a time period for alternating between the first potential and the second potential is past.

7. The method of claim 5 wherein the time period for alternating between the first potential and the second potential is no more than 500 milliseconds.

8. The method of claim 5 wherein the time period for alternating between the first potential and the second potential is no more than 100 milliseconds.

9. The method of claim 1 wherein the electrocatalyst catalyzes a redox reaction of a second target gas, different from the first target gas, at the second potential and the electrocatalyst is substantially inactive to catalyze the redox reaction of the second target gas at the first potential, the method further comprising:

measuring a second output signal arising from the redox reaction of the second target gas at the second potential; and deconvoluting the second output signal while the at least one working electrode is biased at the second potential to separate a portion of the second output signal arising from non-faradaic current to determine a concentration of the second target gas.

10. The method of claim 9 further comprising deconvoluting the first output signal while the at least one working electrode is biased at the first potential to separate the portion of the first output signal arising from non-faradaic current to determine a concentration of the first target gas each of the plurality of times the potential of the working electrode is biased to the first potential and deconvoluting the second output signal while the at least one working electrode is biased at the second potential to separate the portion of the second output signal arising from non-faradaic current to determine a concentration of the second target gas each of the plurality of times the potential of the working electrode is biased to the second potential.

11. The method of claim 10 wherein the ratio of total electrochemically accessible surface area to geometrical surface area is at least 10:1.

12. The method of claim 10 wherein the ratio of total electrochemically accessible surface area to geometrical surface area is at least 200:1.

13. The method of claim 11 wherein the first output signal is deconvoluted while the at least one working electrode is biased at the first potential and after at least 95% of a time period for alternating between the first potential and the second potential is past and the second output signal is deconvoluted while the at least one working electrode is biased at the second potential and after at least 95% of a time period for alternating between the first potential and the second potential is past.

14. The method of claim 11 wherein the first output signal is deconvoluted while the at least one working electrode is biased at the first potential and after at least 99% of a time period for alternating between the first potential and the second potential is past and the second output signal is deconvoluted while the at least one working electrode is biased at the second potential and after at least 99% of a time period for alternating between the first potential and the second potential is past.

15. The method of claim 13 wherein the time period for alternating between the first potential and the second potential is no more than 500 milliseconds.

16. The method of claim 13 wherein the time period for alternating between the first potential and the second potential is no more than 100 milliseconds.

17. The method of claim 1 wherein deconvoluting the first output signal while the at least one working electrode is biased at the first potential to separate a portion of the first output signal arising from non-faradaic current comprises subtracting a baseline non-faradaic signal determined in the absence of the first target gas.

18. The method of claim 9 wherein deconvoluting the first output signal while the at least one working electrode is biased at the first potential to separate a portion of the first output signal arising from non-faradaic current comprises subtracting a baseline non-faradaic signal determined in the absence of the first target gas and deconvoluting the second output signal while the working electrode is biased at the second potential to separate a portion of the second output signal arising from non-faradaic current comprises subtracting the baseline non-faradaic signal determined in the absence of the first target gas.

19. An electrochemical gas sensor comprising:

at least one working electrode comprising an electrocatalyst and having a ratio of total electrochemically accessible surface area to geometrical surface area of at least 2:1, circuitry to bias the at least one working electrode to a first potential at which the electrocatalyst catalyzes a redox reaction of a first target gas and bias the at least one working electrode to a second potential, different from the first potential, at which the electrocatalyst is substantially inactive to catalyze the redox reaction of the first target gas, and a system to deconvolute an output signal when the at least one working electrode is biased at the first potential to separate a portion of the output signal arising from non-faradaic current to determine a concentration of the first target gas.

* * * * *